US 6,581,038 B1

(12) United States Patent
Mahran

(10) Patent No.: US 6,581,038 B1
(45) Date of Patent: Jun. 17, 2003

(54) AUTOMATED PROFILER SYSTEM FOR PROVIDING MEDICAL INFORMATION TO PATIENTS

(75) Inventor: Howard E. Mahran, Duvall, WA (US)

(73) Assignee: Nexcura, Inc., Seattle, WA (US)

( * ) Notice: Subject to any disclaimer, the term of this patent is extended or adjusted under 35 U.S.C. 154(b) by 0 days.

(21) Appl. No.: 09/268,122

(22) Filed: Mar. 15, 1999

(51) Int. Cl.⁷ .............................................. G06F 17/60
(52) U.S. Cl. ...................... 705/3; 705/1; 705/2; 707/3; 707/5; 707/101; 707/104.01; 709/203; 706/902; 706/924; 128/923; 600/300
(58) Field of Search ...................... 705/1, 2, 3; 707/3; 707/5, 101, 104.01; 709/203; 706/924; 128/923; 600/300

(56) References Cited

U.S. PATENT DOCUMENTS

| | | | |
|---|---|---|---|
| 4,528,643 A | 7/1985 | Freeny, Jr. ................... 705/52 |
| 4,733,354 A | 3/1988 | Potter et al. ................ 600/300 |
| 4,839,822 A | 6/1989 | Dormond et al. ............ 706/45 |
| 5,225,976 A | * 7/1993 | Tawil ............................. 705/2 |
| 5,299,121 A | * 3/1994 | Brill et al. ................... 600/301 |
| 5,341,291 A | * 8/1994 | Roizen et al. .............. 600/300 |
| 5,517,405 A | * 5/1996 | McAndrew et al. .......... 706/45 |
| 5,583,758 A | 12/1996 | McIlroy et al. .............. 705/2 |
| 5,586,024 A | 12/1996 | Shaibani ..................... 600/300 |
| 5,594,638 A | 1/1997 | Iliff .............................. 703/3 |
| 5,660,176 A | 8/1997 | Iliff ............................ 600/300 |
| 5,664,109 A | * 9/1997 | Johnson et al. ................ 705/2 |
| 5,711,297 A | 1/1998 | Iliff ............................ 600/300 |
| 5,724,580 A | 3/1998 | Levin et al. ............. 707/104.1 |
| 5,724,968 A | 3/1998 | Iliff ............................. 600/300 |
| 5,757,917 A | 5/1998 | Rose et al. ................... 705/79 |
| 5,768,528 A | 6/1998 | Stumm ........................ 709/231 |
| 5,915,240 A | * 6/1999 | Karpf ............................. 705/2 |

FOREIGN PATENT DOCUMENTS

WO    WO 99/52025    * 10/1999

OTHER PUBLICATIONS dialog reference, file 15, No. 00867725, Gary K. Johnson, functional requirements of a computer–based patient record system, Healthcare Financial Management v48n6 pp: 54–62, Jun. 1994.*

* cited by examiner

Primary Examiner—Eric W. Stamber
Assistant Examiner—Raquel Alvarez
(74) Attorney, Agent, or Firm—Fish & Neave; Norman H. Beamer

(57) ABSTRACT

Apparatus and methods are disclosed for generating individualized medical profiles based on information provided by a patient, and on data extracted from medical literature. In a first stage, medical literature is selected for inclusion in a database by using specified inclusion criteria. Information on input parameters to studies contained in the literature, output parameters of the studies, and algorithms contained in the studies is extracted from the literature, and stored in a database. In a second stage, patients provide information, which is matched against the input parameters of the studies in the database, and algorithms from the matched studies are applied to the information provided by the patient to produce values for the output parameters. Combination analysis is used to combine the values of output parameters into "supercategory" values, that are used to generate an individualized medical profile.

43 Claims, 10 Drawing Sheets

AUTOMATED PROFILER SYSTEM FOR PROVIDING MEDICAL INFORMATION TO PATIENTS

FIELD OF THE INVENTION

The present invention relates generally to methods and apparatus for collecting medical data, and for providing a patient with customized access to the data. More specifically, the present invention provides a computerized profiler system for building a medical database from medical literature, and automatically generating personalized profiles based on information provided by a patient and medical data stored in the medical database.

BACKGROUND OF THE INVENTION

As medical information resources have become easier to access, the public demand for such resources has increased. The Internet has enabled millions of users worldwide to access an ever-growing selection of medical information, and has resulted in patients becoming increasingly knowledgeable about their medical conditions. Additionally, the Internet has provided patients with access to world-wide on-line communities of individuals with similar medical conditions, who are able to share their experiences and advice.

While this increase in the availability of medical information to patients has had some good effects, such as a heightened level of discussion between physicians and patients, it also has some drawbacks. Much of the information available to patients over the Internet is unreliable. It is often based on individual experiences or opinions, rather than on solid medical research. Such material can mislead patients, or even cause additional medical difficulties if unreliable advice is followed without first consulting a physician.

Even medical information provided by reliable on-line sources may not be helpful. Much of the information that is available is highly technical, and is not comprehensible to most patients. Reliable information that is written for use by patients who do not have extensive medical knowledge is often too general to be useful, and may not include information on the latest research and treatments. Additionally, almost all of the information available to patients over the Internet is generic, in that it is not specifically tailored to the individual patient's medical conditions.

At the same time that patients are gaining access to medical information, medical knowledge is growing at an ever increasing rate. Each month, dozens of studies on a variety of diseases and treatments are published in numerous credible medical journals. The volume of information published each year on some major diseases, such as cancer, is becoming so great that even specialists in the field may be unable to keep up with all the latest research. Without knowledge of the latest research and techniques, a physician may not be able to render the best possible advice to his or her patients.

This difficulty in rendering the best advice is further compounded by the fact that many patients are becoming more sophisticated in the demands that they place on physicians, as discussed above. Physicians may have difficulty keeping up with the latest information that will be required to satisfy knowledgeable patients, who may have detailed questions pertaining to recent research and techniques.

There have been many attempts to provide automated systems for generating individualized medical diagnoses or advice. A couple of recent examples are shown in U.S. Pat. No. 5,711,297, to Iliff, which provides automated medical advise to the general public over a telephone, and U.S. Pat. No. 5,724,580, to Levin et al., which assists physicians by automatically generating individualized management and prognosis reports.

Typically, these systems ask the patient (or physician) a series of questions, or require that data about a patient's condition be entered into a computer. This information is processed by applying a set of rules to the data, which results in the system generating diagnoses or advice.

One difficulty with such systems is that the rules are often static, and are based on the knowledge of one or more physicians, or gleaned from medical textbooks on the field to which the rules pertain. Thus, the rules depend on the specific knowledge of a few individuals, or on general medical knowledge, rather than being based on the latest research. Since the rules tend to be static, either contained in a database of rules or hard-coded into the system, it may be difficult to update the rules based on new research.

Even in systems where the rules are not static, there is no way of entering the results of the latest medical research, other than updating the rules. Since the rules in these systems are typically complex and interrelated, a change in one rule may lead to many changes in the rule base. Thus, changing a few rules to account for the latest research may lead to many changes in the rules on which a system operates.

A few systems have rejected a rules-based approach, in favor of a more dynamic method. U.S. Pat. No. 5,586,024, to Shaibani, for example, matches accident factors for a current patient against accident factors from past accidents to diagnose possible trauma injuries. By basing a diagnosis on past results, this approach permits the system to be automatically updated based on its most recent experiences. Since the system is not rule-based, it is not necessary to derive and enter a complex set of rules. However, because the (system described in Shaibani depends on experience, rather than knowledge, reports generated by the system are not based on medical research.

Both rules-based systems and those that use some other approach typically focus on providing a medical diagnosis or medical advice, rather than on providing medical information. Rather than attempting to augment the patient's or physician's knowledge, most known systems attempt to replace or augment a physician's judgement in making a diagnosis. For example, most systems do not provide citations to medical papers that may be helpful or relevant to the individual patient or his/her physician.

In view of the above, it would be desirable to provide an automated system that generates individualized medical information for a patient based on information provided by the patient, and on knowledge extracted from medical research literature.

It would further be desirable to provide methods and structures for extracting and storing useful results or other information from medical literature.

It also would be desirable to provide automated methods for applying medical knowledge stored in a medical database to provide a patient with individualized information on a variety of treatment options that may be discussed with a physician.

SUMMARY OF THE INVENTION

It is an object of the present invention to provide an automated system that generates individualized medical information for a patient based on information provided by the patient, and on knowledge extracted from medical research literature.

It is a further object of the present invention to provide methods and structures for extracting and storing useful results or other information from medical literature.

It also is an object of the present invention to provide automated methods for applying medical knowledge stored in a medical database to provide a patient with individualized information on a variety of treatment options that may be discussed with a physician.

These and other objects of the present invention are achieved by providing a system that stores information extracted from medical literature in a medical database, and uses the information in the database, along with information provided by a patient, to generate an individualized medical profile, containing information on available treatments, as well as information on the medical literature that was used to generate the treatment information.

In a preferred embodiment of the system of the present invention, a medical database is stored on a server computer, and patients interact with the server computer over the Internet. A user connects to the system over the Internet using a standard web browser, and interacts with the system by filling out one or more forms that request specific information from the user. The system then uses a medical database, built using information from the medical literature, to generate an individualized profile for the patient. In a preferred embodiment, the individualized profile is displayed in the web browser, and the patient may select links in the individualized profile to access more detailed information on the medical literature that was used to generate the profile.

The system of the present invention includes two major components: extraction of information from medical literature to build a medical database; and a series of programmed routines that use the medical database, along with information provided by a patient, to generate an individualized profile.

Preferably, an editorial review board made up of specialists in numerous medical fields is assembled to review and score medical literature for inclusion in the medical database. Based on predetermined criteria, the review board determines which papers and studies should be used to generate a database of medical information for a specific disease state, e.g., prostate cancer. The review board continually evaluates new medical literature, and adds new studies to the medical database. In this way, the information in the medical database is continually updated to reflect the latest research.

Studies that are accepted for inclusion in the database go through a data extraction process in which useful information and algorithms from the papers are extracted and stored in various tables in the medical database. Input parameters, output parameters, data tables, information on the study population, statistical information, and any appropriate algorithms employed in the paper, together with an abstract, and citation information are extracted from each study. Additionally, each study is assigned an output category, based on the function served by the output of the study, a treatment category, based on the treatment applied in the study, and a combination rule, which is used to combine output from the study into "super-categories". All of this information, as well as information on available treatments and their indications are stored in the medical database.

The second component of the system comprises a series of programmed routines constructed in accordance with the present invention that use the medical database to generate customized profiles for patients. A patient provides various personal and clinical information to the system as input. If there is any missing information, the system provides a missing information report to the patient. Next, the database is used to match the available information against the input parameters for each of the studies in the medical database. Algorithms or tables extracted from all studies for which the input parameters were matched are applied to the information provided by the patient to generate output data. Combination analysis is then performed on the output data to combine the output from the various studies into predetermined "super-category" values.

Next, information on treatments and their indications stored in the medical database is applied to the information provided by the patient, and to the "super-category" values, to determine which treatments are most applicable. For each of the treatments, the information provided by the patient, as well as the combined "super-category" values, and the output from the studies are used in conjunction with the studies in the medical database that pertain to the outcome of the treatment to generate information on the probable outcome of each treatment.

All of the information on the input provided by the patient, the output data from the studies, the "super-category" values, the indicated treatments, the probable treatment outcomes, and the studies that were applied are combined to generate a personalized profile. The personalized profile is then made available to the patient. The patient is advised to discuss the profile with a physician, who may be able to assist the patient in assessing the profile, and may provide additional information to the system. As the patient adds or changes the input data, the system may be employed to generate updated personal profiles.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

The present invention provides a system for generating individualized disease and treatment profiles for patients. The system comprises two stages: a first stage, in which medical data are collected from numerous sources to assemble a medical database; and a second stage, in which the database is used in conjunction with information provided by a patient to generate individualized profiles. The system is described hereinbelow using an example embodiment for gathering data on prostate cancer, and for providing individualized reports to prostate cancer patients. It will be apparent to one skilled in the art that the system is general, and could be readily applied to nearly any disease or medical condition.

Definitions

For the purpose of describing the system of the present invention, it is useful to define several terms. As used hereinbelow, a "study" refers to the results of medical research, typically involving numerous human subjects. A study has input parameters, which identify the variable factors in the study, and output parameters, which identify factors that are affected by variation in the input parameters. A study can be seen as defining a function or algorithm that maps values of the input parameters to values of the output parameters.

As used hereinbelow, a "paper" is a publication or other source of medical information that contains one or more studies. Papers are typically published in medical journals, but also may come from other sources, such as conference proceedings, textbooks, tutorials, research reports, or any other type of medical literature.

A database, as used hereinbelow, is a compilation of data stored on a computer system. A database may contain datasets and tables. A dataset is a collection of related data, and may contain one or more interrelated tables. A table is also a set of related data organized into one or more fields. Each field identifies a specific piece of data, such as a unique identifier, or a description. Some fields may contain references to other tables in the database, to entire datasets, or to specific records or fields in any table in the database. Additionally, fields may contain pointers to data stored in other databases, available either on the same computer, or accessible over a network.

A unit of data in a table is referred to as a record. Thus, a record in a particular table comprises data populating each of the fields associated with the table. A record set is a grouping of records, such as all the records of a particular table, or all the records that match a particular query.

Overview

Figure 1A:
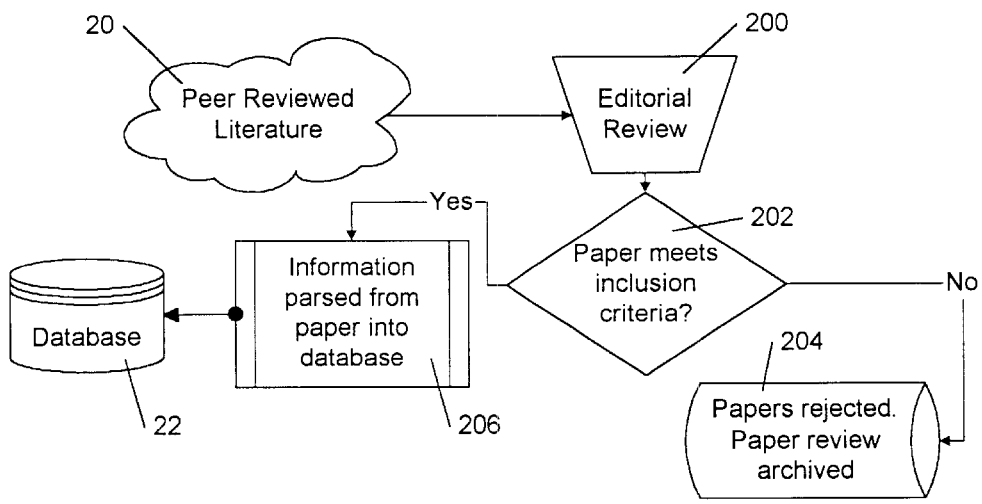
FIGS. 1A and 1B are overviews of the two major components of the system of the present invention.

Referring to FIG. 1A, an overview of a first stage of a system constructed in accordance with the principles of the present invention is described. In this stage, medical data are collected to create a medical database. Peer-reviewed papers 20 are provided to an editorial review board, which reviews papers 20 at step 200 to determine which papers should be included in the database.

At step 202, each individual paper that has been reviewed is checked to see if it meets predetermined inclusion criteria, and should be included in the database. If the paper does not meet the inclusion criteria, the review of the paper is archived at step 204, and the paper is not included in the database. Otherwise, if the paper meets the inclusion criteria, information on any studies contained in the paper is extracted in step 206, and the extracted information is stored in database 22.

Figure 1B:
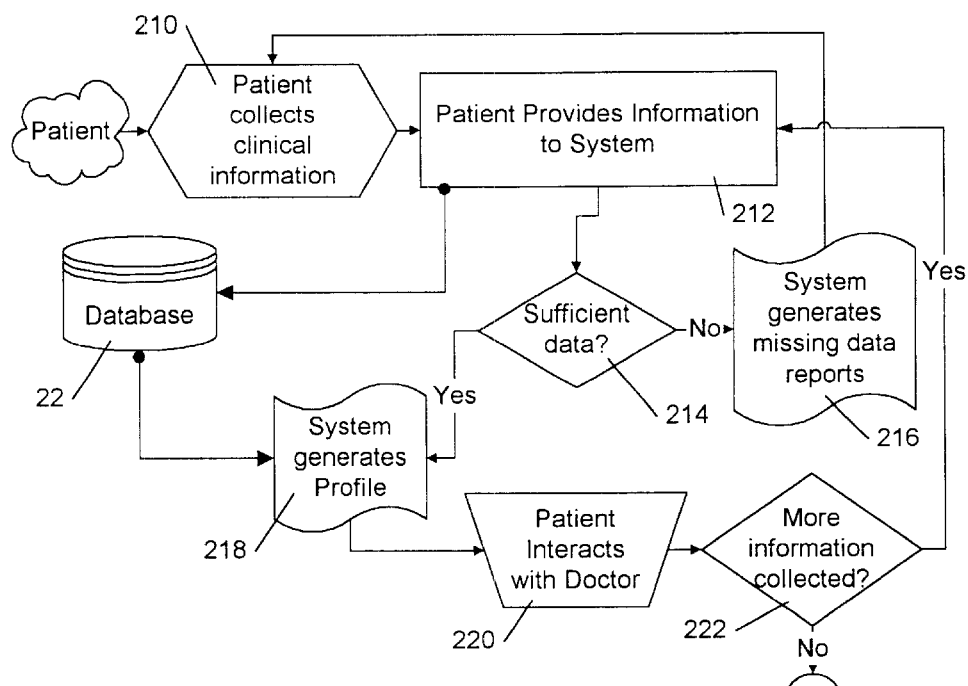

Once a sufficient quantity of medical data is available in database 22, a second stage of the system of the present invention, described with respect to FIG. 1B, may be used. This second stage permits individualized profiles to be generated for patients, based on information provided by the patients and on the data in database 22.

At step 210, the patient collects a variety of clinical information, such as results of medical tests, and information provided by a physician. At step 212, the patient provides this clinical information, as well as demographic information, and information relating to quality of life issues to a computer executing software designed in accordance with the principles of the present invention. The information is provided through an interactive process, e.g., by having the patient visit an Internet site. Alternatively, the patient may interact with the computer over a telephone, using voice or touch-tone commands, or through fax or mail, by sending forms containing the information. Data provided by the patient is stored in a patient dataset in database 22.

At step 214, the system evaluates the data provided by the patient to determine if there is sufficient data to produce an individualized profile. If the system determines that there is not yet enough patient data, it generates a "missing data report," at step 216, which is sent to the patient, e.g., as either an additional screen display, e-mail message, or computer-generated form mailing. The missing data report tells the patient what data is needed before a profile may be generated.

When the patient has provided sufficient information, the system uses the information in step 218, along with medical data from database 22, to generate an individualized profile. The profile contains assessments of available treatment options, any common complications associated with each of the treatment options, and the likely results of each of the options when applied to the individual patient. Additionally, the profile may contain information on quality of life issues related to each of the treatment options, and information on the experiences of other patients who have used each option.

In a preferred embodiment, the completed profile is sent to the patient over the Internet, in an interactive format that permits the patient to request further information, or specific details of the report. Alternatively, the report may be sent over the Internet in a non-interactive format, such as e-mail, or via fax, or through the mail. At step 220, the patient reviews the report with his or her physician. As additional clinical information is collected, or if the patient's condition changes or progresses, this information may be provided to the system (step 222), which can then generate updated profiles by repeating the above-described process.

Stage I: Building the Medical Database

Study Selection

Figure 2:
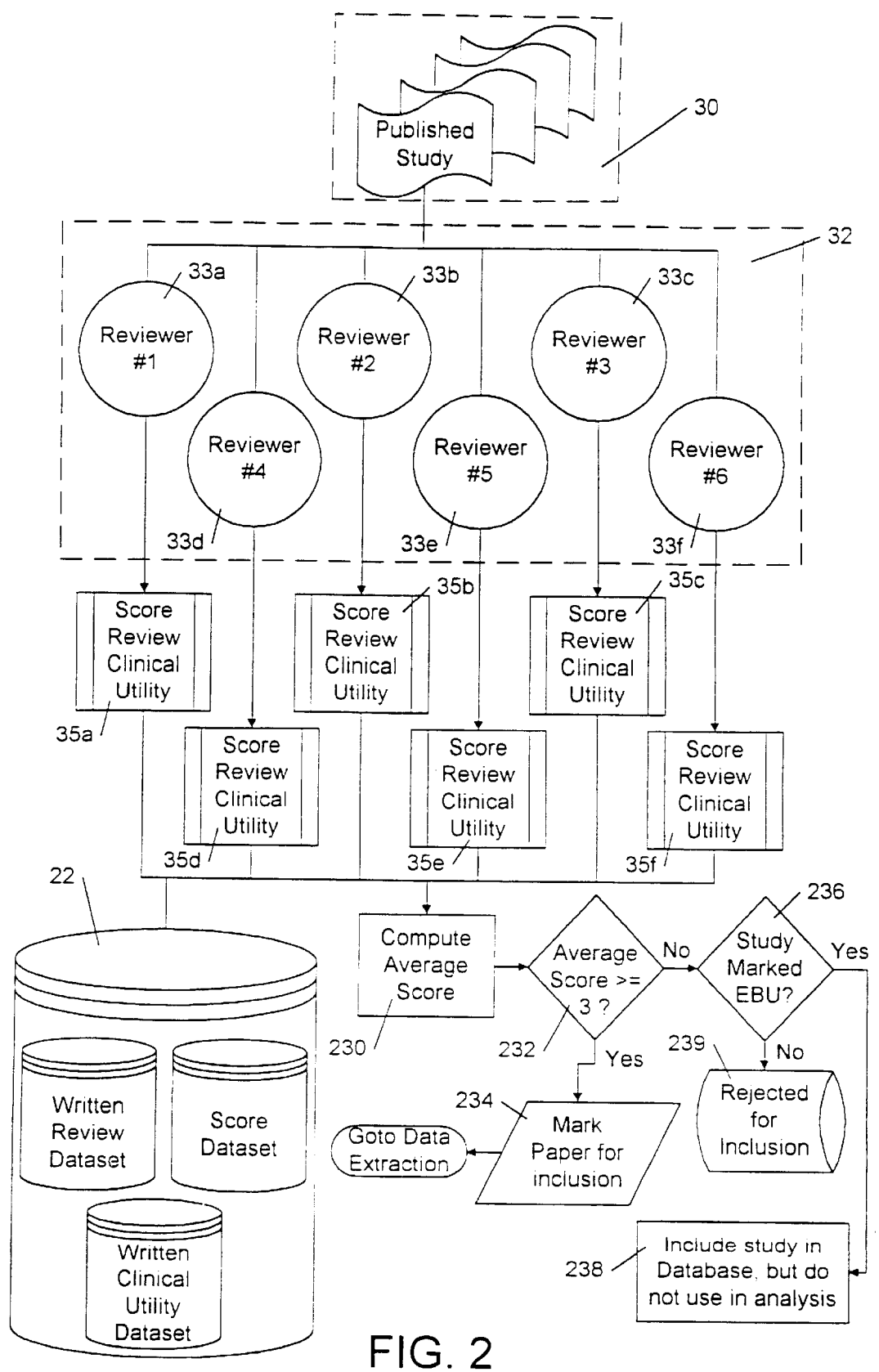
FIG. 2 is a detailed flowchart of the method for selecting studies for inclusion in the medical database.

Referring to FIG. 2, a preferred procedure for reviewing papers, and for deciding which papers should be included in database 22 is described. Medical papers 30 are gathered and reviewed by medical editorial board 32. Medical editorial board 32 comprises reviewers 33a–f, each of whom is preferably a medical expert or specialist in a field of medicine related to the specific disease and treatments for which database 22 is being constructed. Additionally, each medical editorial board preferably includes at least one pathologist, and a statistician. In an illustrative embodiment in which database 22 contains data on cancer, numerous medical editorial boards, one for each major cancer type (e.g. prostate, breast, bladder, etc.), will be assembled. The medical editorial board for prostate cancer, for example, may include specialists such as urologists, uropathologists, seed implant specialists, medical oncologists, radiation oncologists, and statisticians.

Each medical review board 32 is responsible for locating and reviewing papers that may be included in database 22. During an initial review, papers that contain information or studies that may be useful are identified as candidate papers. Each candidate paper or study is then reviewed for inclusion, preferably using the following inclusion criteria:

(1) Are the objectives of the paper clearly stated and understood by the reviewer?;
(2) Is the study population detailed adequately in the materials section?;
(3) Are the methods described well enough to reproduce the experiment or investigation?;
(4) Can the reviewer assess the results based on the data provided?;
(5) Has there been a statistical evaluation of the data that shows statistical significance?;
(6) Are there results that are statistically significant that can be summarized in a table or equation?; and
(7) If this paper does not meet the criteria above, should it be marked as "experimental but useful" (EBU)? Papers marked as EBU will be included in the database, but not included in the final analysis process.

Based on the foregoing inclusion criteria, members 33a–f of medical editorial board 32 prepare summaries 35a–f for each paper or study. These summaries contain written reports and clinical utility reports for each paper or study, and assign each paper or study a numerical score, preferably ranging from 1 to 5. In a preferred numerical rating system, a score of 1 indicates that the paper is useless, a score of 2 indicates that the paper does not contain sufficient study data, a score of 3 indicates that the paper contains sufficient study data, a score of 4 indicates an excellent paper, and a score of 5 indicates that the paper sets the standard of care for the disease in question. Summaries 35a–f are stored in database 22, with the written reviews, numerical scores, and clinical utility reports for each paper or study being stored in a written review dataset, a score dataset, and a written clinical utility dataset, respectively.

At step 230, the numerical scores from summaries 35a–f are averaged. If the average score is 3 or greater (step 232), the paper is marked for inclusion in database 22, and for use in the analysis process (step 234). Papers that receive an average score lower than 3 are checked to see if the majority of the reviewers marked the paper as "Experimental but Useful" (EBU) (step 236). If so, the paper is included in database 22 (step 238), but will not be used in the analysis process. Papers that did not receive a score of 3, and that are not EBU are rejected at step 239.

Once the useful papers have been identified, data must be extracted from them to be placed in database 22, and to be used in the analysis process. Before describing the extraction process in detail, it is necessary to describe the structure of the datasets and tables in database 22 in which the data from the papers and studies are stored.

Structure of the Literature Dataset

Figure 3:
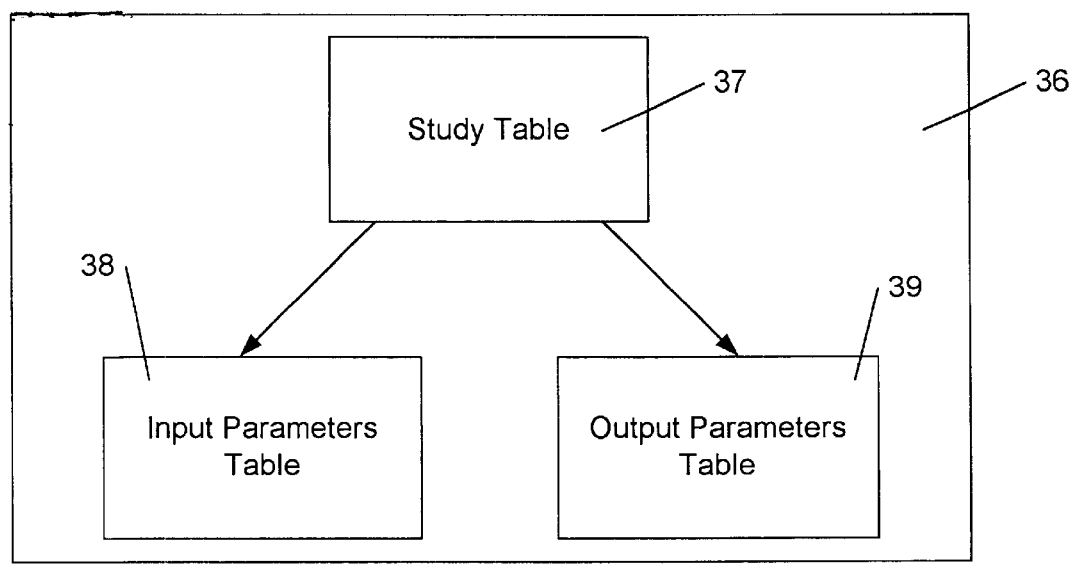
FIG. 3 is an overview of the structure of the literature dataset in the medical database.

Referring to FIG. 3, a high-level overview of literature dataset 36 of database 22 is described. Literature dataset 36 preferably includes study table 37, containing data related to the medical studies stored in database 22. Study table 37 includes fields that point to input parameters table 38, which stores data on the input parameters associated with each study, and output parameters table 39, which stores data on the output parameters of each study.

Figure 4:
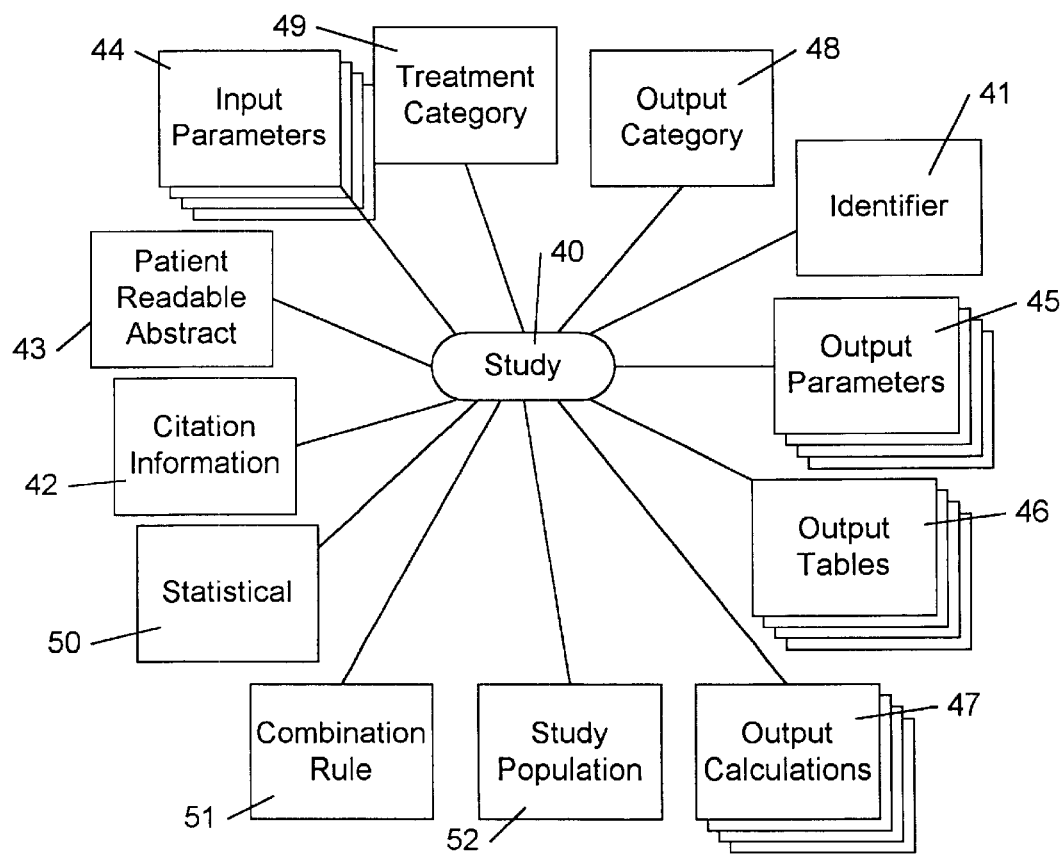
FIG. 4 shows the structure of a record in the study table of the literature dataset in the medical database.

FIG. 4 shows the anatomy of a record in study table 37 of literature dataset 36 in database 22. Study record 40 has data in fields representing the input parameters of the study, the output parameters of the study, tables and calculations provided by the study, the study's output and treatment categories, citation information, and a patient-readable abstract of the study.

Identifier field 41 contains a unique identifier for each record in study table 37. Fields in other tables that reference records in study table 37 may use the values stored in identifier field 41 to point to a particular record in study table 37.

Citation information field 42 contains information on the title of the paper or study, the author, the journal in which the study appeared, the page numbers in the journal, the publication date, or any other information that is needed to identify the source from which the data in a study record was extracted. As will be understood by one skilled in the art, this field may either contain all these items directly (as subfields), or, in a preferred embodiment, may point to records in a "literature citation" table (not shown) having fields for the various parts of the citation information.

Patient readable abstract field 43 contains the text of an abstract of the study from which the data in study record 40 was extracted. This abstract may be displayed or printed as part of an individualized profile, to provide the patient with information on the papers or studies that were used to prepare the profile.

Input parameters field 44 contains a list of one or more input parameters for the study. Each entry in the list points to a record in input parameters table 38, described in greater detail hereinbelow. It should be noted that numerous study records may point to the same input parameter. Thus, for example, if numerous studies require an input parameter representing the percent of cancer in a biopsy, the records for all of these studies may point to a single "percent of cancer in biopsy" record in input parameter table 38.

Output parameter field 45 contains a list of one or more output parameters for the study, each of which points to a record in output parameters table 39, described in detail hereinbelow. Although multiple studies may point to the same record in output parameter table 39, due to subtle variations in the precise meaning of the "same" output parameter in different studies, this may be less common than for input parameters.

Output tables field 46 contains zero or more tables that specify algorithms for mapping values of input parameters to values of output parameters. These tables are derived from the study, and may be multi-dimensional, providing a value for an output parameter based on the values of multiple input parameters. Additionally, as will be understood by one skilled in the art, structures such as neural networks or fuzzy logic algorithms may be represented in tables. When the results of a study are amenable to using such techniques, the tables representing the necessary structures may be stored in output tables field 46.

Similarly, output calculations field 47 contains zero or more calculations derived from the study that specify algorithms for mapping values of one or more of the input parameters to values for one or more of the output parameters. The results from some studies are better represented by a function or calculation than by a table. These functions or calculations, preferably represented as code for computing the function, are stored in output calculations field 47. The code stored in output calculations field 47 may be written in any computer language in which mathematical functions may be expressed, such as C++, Java or Javascript. Additionally, it should be noted that for studies that are useful in generating individualized profiles, either output calculations field 47 or output tables field 45 should contain at least one entry.

Output category field 48 contains the identifier of an output category to which the study is directed. For example, in a system for providing profiles to prostate cancer patients, a study that addresses determination of the pathologic stage of the cancer would have a "staging" output category, whereas a study directed to predicting disease free survival would have an "outcome" output category. The available output categories for an illustrative prostate cancer system should preferably include a staging category, for studies directed to determining the pathologic staging of the cancer; an outcome category, for studies directed to predicting disease free survival or PSA recurrence; a quality of life category, for studies directed to quality of life issues, such as incontinence or impotence; a complications category, for studies directed to complications that may occur as a result of treatment; and an alternatives category, for studies relating to alternative and integrative medicine.

Treatment category field 49 contains information on any treatment that the study population received. This information permits the output category to be related to the treatment. For example, a study may provide information on the 36 month disease free survival rate for patients who underwent radical prostatectomy. For this study, the output category would by "outcome" (see above), and the treatment category would be "radical prostatectomy." Treatment categories for the prostate cancer example system preferably include radical prostatectomy, seed implants, chemotherapy, cryotherapy, external beam radiation, conformal beam radiation, watchful waiting, hormonal blockade, alternative, and hyperthermia.

Statistical field 50 contains any statistical information found in the study. Studies may, for example, contain information on p-values, the mean value of a parameter within the study population, standard deviation, population distribution, the median within the study population, the sensitivity, or the specificity. Any such information relating to study statistics should be stored in statistical field 50.

Combination rule field 51 identifies the combination analysis method that will be used to combine output parameters into a super-category value (described hereinbelow) for this study. Combination analysis methods may include simple methods, such as averaging, more complex methods, such as fuzzy logic or fuzzy sets, statistical methods, such as meta-analysis, or interactive techniques. The availability of some of these techniques may depend on the nature of the statistical information that is available in statistical field 50. For example, for meta-analysis to be used, statistical field 50 must include either p-values, means and standard deviations, or population distributions.

Study population field 52 contains information on the group of subjects on whom the study was conducted. As a minimum, study population field 52 contains the size of the study population. For example, if the study was conducted using a population of 780 people, study population field 52 would contain 780 as the size of the study population. This information is used when generating reports.

Figure 5:
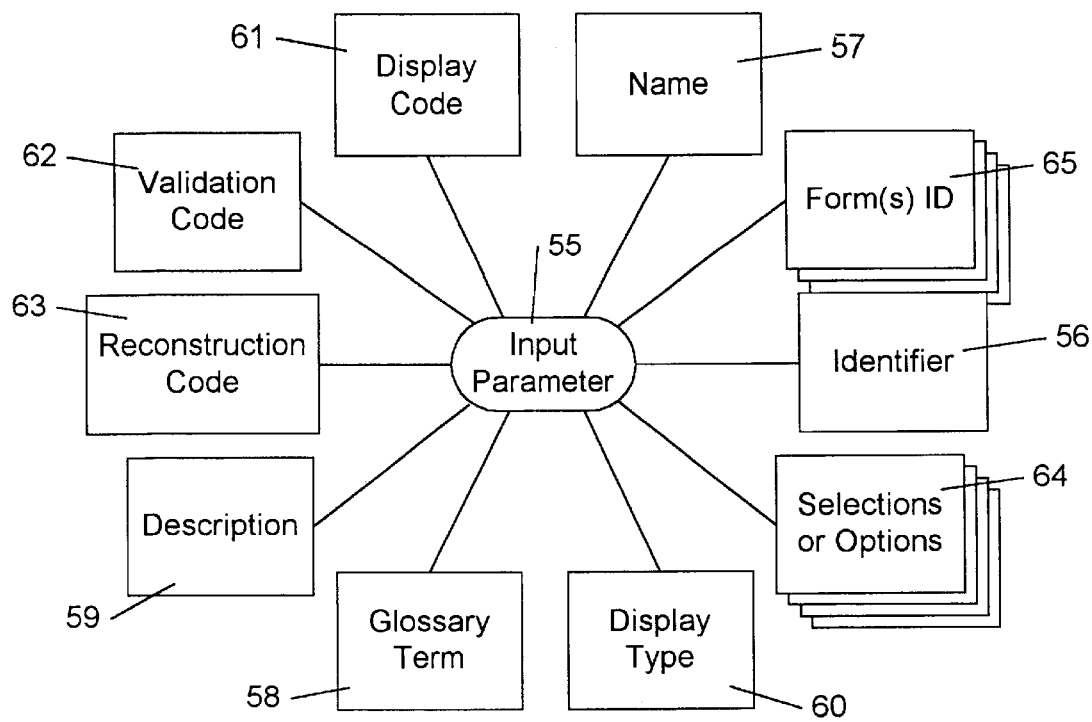
FIG. 5 shows the structure of a record in the input parameters table of the literature dataset in the medical database.

FIG. 5 shows the structure of a record in input parameters table 38 of literature dataset 36 of database 22. Records in input parameters table 38 are used to describe the input parameters of studies. Input parameter record 55 preferably includes fields containing an input parameter identifier, the display type for the input parameter, a glossary term and description of the input parameter, code for displaying, validating, and reconstructing values of input parameters, information on which input forms are used to obtain values for the input parameter, and available selections or options for the input parameter.

Identifier field 56 contains a unique identifier for each record in input parameters table 38. Fields in other tables (such as study table 37) that reference records in input parameters table 38 may use the values stored in identifier field 56 to point to a particular record in input parameters table 38.

Name field 57 contains the name of the input parameter. This name will be displayed on an input form used for gathering information from a patient.

Glossary term field 58 contains the text of a detailed description of the input parameter that may be used to assist a user in providing values for the input parameter. Similarly, description field 59 contains the text of a short description of the input parameter, for users in need of quick help. As will be described in greater detail hereinbelow, the text in description field 58 may pop up automatically in an input form that is used to provide a value for the input parameter.

Display type field 60 contains information on the display type of the input parameter. For example, the input parameter might be a percentage, a date (mmddyy), a yes or no answer, an integer, or any other type. Display type field 60 identifies the type of the input parameter.

Display code field 61 contains code, e.g., written in HTML, for displaying the input parameter on a web page or form. When it is necessary to display an input parameter, the display code for that parameter is executed.

Validation code field 62 contains code, e.g., written in Javascript, for validating an input parameter. When a user enters a value for an input parameter, the validation code is executed to make sure that the user has entered a valid value for the parameter. For example, if an input parameter is expressed as a percentage, the valid values range from 0 to 100. If a user entered 470, the validation code would reject the input. In some cases, the validation code also converts data entered by the user into an internal format. For example, a user may enter a date as three separate numerical values—a month, day, and year. Since a date may be stored internally as a single number, the validation code must convert the format of the user's input (three values) to the single number representing the date entered by the user.

Reconstruction code field 63 contains code, preferably written in Javascript, for converting values of the input parameter from an internal format to a format for display. Thus, using the date example, the reconstruction code may be executed to convert a date that is stored internally as a single number into three numbers, a month, day, and year. Typically, the code contained in reconstruction code field 63 is executed whenever the value of the input parameter must be displayed. If the value is being displayed on a web page or form, the code is executed before the code contained in display code field 61.

Advantageously, these code fields permit all the code necessary to display, validate, and reconstruct the input parameter to be encapsulated with other data on the input parameter in database 22. Thus, an input parameter may be seen as an object that "knows" how to display itself, how to check its input for valid values, and how to convert itself between internal formats and user-readable formats. This also permits the system to automatically generate forms for use in gathering information from patients, as will be described in greater detail hereinbelow.

Selections field 64 contains a list of selectable values for the input parameter if the input parameter is of a type for which such selectable values are appropriate. For example, if the input parameter is a "True" or "False" selection, selections field 64 will contain a selection for true, and a selection for false. Similarly, an input parameter associated with quality of life could have selections for "incontinence is acceptable", "incontinence should be avoided", and "incontinence is unacceptable." Selections in selections field 64 are each associated with a value for the input parameter, and will appear in a drop-down list in a user input form.

Form(s) ID field 65 contains a list of one or more forms on which the input parameter should be included. Each of the input parameters may appear on one or more user input forms. Examples of forms for the prostate cancer system include a blood tests form, a doctor's exam form, an imaging workup form, a demographics form, a quality of life issues form, and a comorbid issues form. In addition to storing information on the forms in which an input parameter is included, a separate table (not shown) for each form may be built, including the identifiers of each of the input parameters that are included in the form, and the order in which the input parameters appear. This information is used to generate user input forms, as described hereinbelow.

Table 1 contains an illustrative list of input parameters used by an illustrative system constructed in accordance with the present invention for generating profiles for prostate cancer patients. Many of these input parameters were extracted from literature, while some, such as birth date, doctor name, telephone number, and address, provide administrative information on the patient. It will be of course be understood that the selection of input parameters in input parameters table 38 will vary according to the disease being handled by the system, and the selection of studies that have been entered into the system. Thus, the input parameters listed in Table 1 are illustrative only, and do not represent all possible input parameters that may be used by a prostate cancer system, since the list changes as a result of the dynamic process of adding studies to the system.

Figure 6:
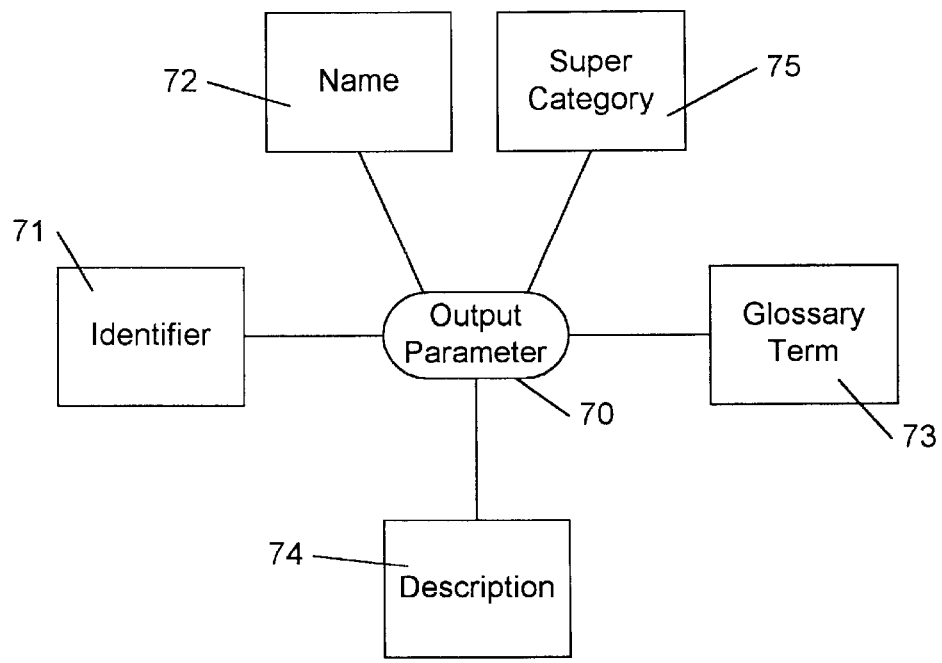
FIG. 6 shows the structure of a record in the output parameters table of the literature dataset in the medical database.

Referring to FIG. 6, the structure of a record in output parameters table 39 of literature dataset 36 of database 22 is shown. Records in output parameters table 39 are used to describe the output parameters of studies. Output parameter record 70 preferably includes fields containing an output parameter identifier, a glossary term and description of the output parameter, and a super-category for the output parameter.

Identifier field 71 contains a unique identifier for each record in output parameters table 39. Fields in other tables (such as study table 37) that reference records in output parameters table 39 may use the values stored in identifier field 71 to point to a particular record in output parameters table 39.

Name field 72 contains the name of the output parameter. This name may be displayed in reports or profiles to identify the output parameter.

Glossary term field 73 contains the text of a detailed description of the output parameter that may be used to assist a user in understanding the meaning of output parameters cited in a profile or report. Similarly, description field 74 contains the text of a short description of the output parameter.

Super-category field 75 contains an identifier of the super-category of the output parameter. Multiple studies addressing the same or similar issues may provide output parameters that are similar or related, but are not identical. For these output parameters to be used in the analysis process, it may be necessary to create a "normalized" form of these output parameters by grouping related output parameters into "super-categories." Related groups of output parameters all have the same super-category, which provides a high level and consistent way for treatment rules (described hereinbelow) and profiles to refer to related output parameters. An example of this hierarchy from the "staging" output category in the prostate cancer system is described with respect to FIG. 7.

Figure 7:
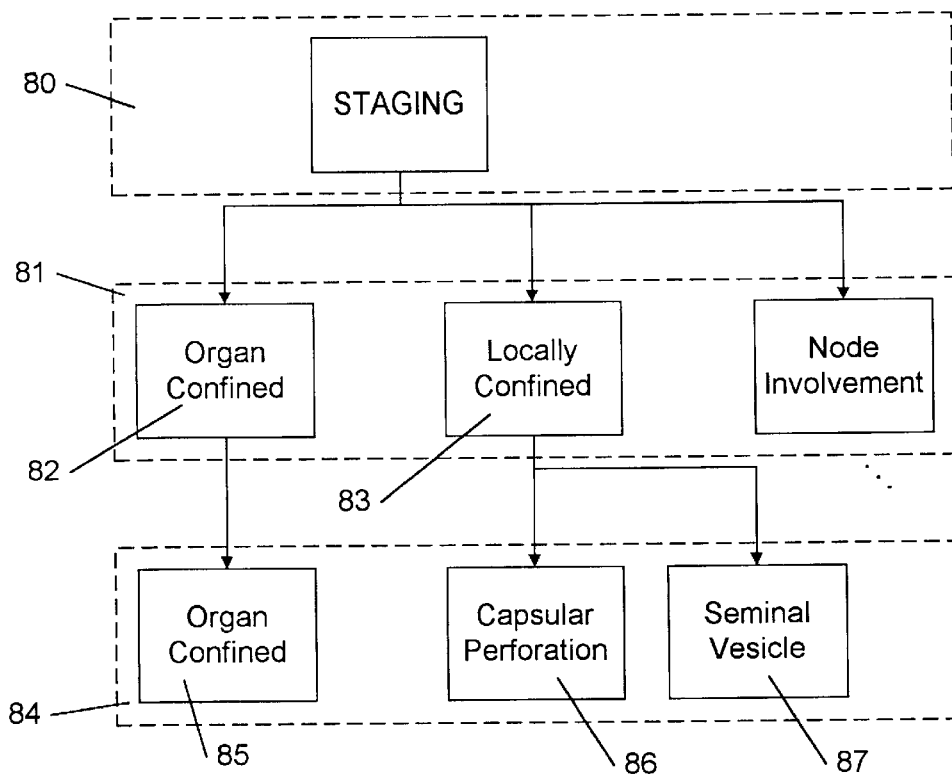
FIG. 7 is an illustrative example of the output parameters and super-categories associated with an output category.

In FIG. 7, top level 80 of the hierarchy represents the output category. In this example, only "staging" is shown, though other output categories also may have related super-categories. Middle level 81 of the hierarchy shows some of the super-categories associated with staging (a more complete list is shown in Table 2). The super-categories includes super-category 82, containing all output parameters relating to whether the cancer is organ-confined, and super-category 83, containing all output parameters relating to whether the cancer is locally confined. Bottom level 84 of the hierarchy contains individual output parameters.

Because "organ confined" output parameter 85 indicates that the cancer is organ confined, its super-category is super-category 72, the "organ-confined" super-category. Both "capsular perforation" output parameter 86 and "seminal vesicle" output parameter 87 are used to determine whether the cancer is locally confined, so both have "locally confined" super-category 83 as their super-category. The values from output parameters 86 and 87 may be combined to create a single "normalized" value for super-category 83, which may be reported in a profile, or used to indicate a treatment.

Table 3 contains an illustrative list of output parameters used by an exemplary system of the present invention for generating profiles for prostate cancer patients. All of the output parameters were extracted from studies. Although there are multiple output parameters with the same name (e.g. 12 Month DFS), these are different output parameters. This is due to differences between studies as to the meaning of output parameters having the same name. Many (but not all) of the output parameters that have the same name are similar, or closely related to each other, and therefore have the same super-category.

Of course, the selection of output parameters in output parameters table 39 will vary according to the disease being handled by the system, and the selection of studies that have been entered into the system. Thus, the output parameters listed in Table 3 are illustrative only, and do not represent all possible output parameters that may be used by a prostate cancer system.

It further will be understood that many of the fields of the study table, the input parameters table, and the output parameters table may be implemented using pointers to records in tables that associate information with ID numbers, rather than using the information itself. For example, the super-category field of records in output parameters table 39 may contain the ID numbers of super-categories, rather than the names of the super-categories themselves. The names of the super-categories may then be listed in a separate table (not shown), in which the names of the super-categories are associated with ID numbers. Most any of the fields in the above-described tables, with the exception of identifier fields, may be implemented in this manner.

Extraction of Data from the Literature

Figure 8:
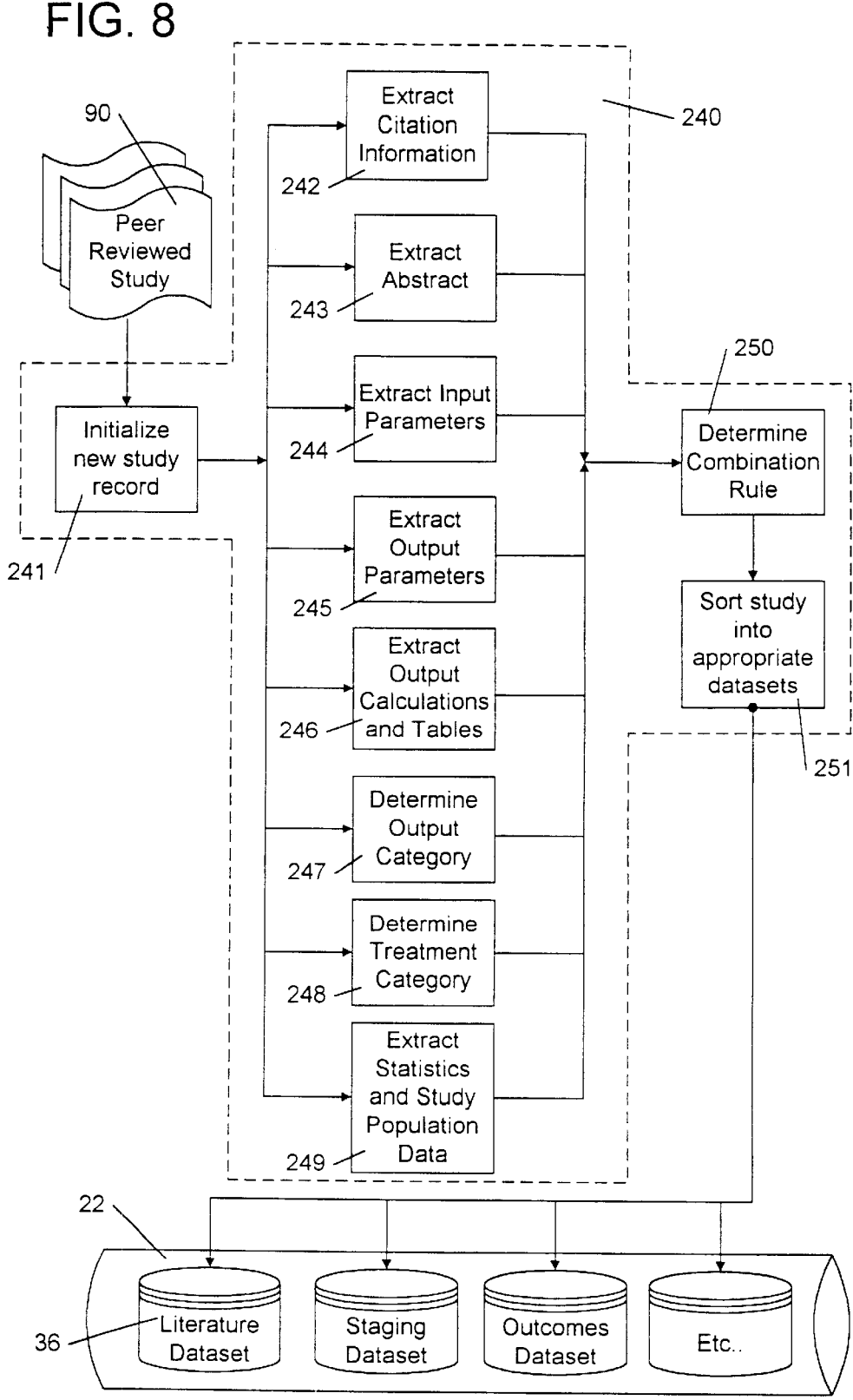
FIG. 8 is a flowchart of the data extraction process.

Referring to FIG. 8, a preferred method for extracting data from studies into database 22 is described. Studies 90 that have met the inclusion criteria are put through the above-described data extraction process (see FIG. 2), in which the relevant data are extracted into a record in study table 37 for inclusion in database 22 (see FIG. 3).

At step 241, a new study record, as described hereinabove with reference to FIG. 4, is prepared to contain information on the study from which data are being extracted. This includes assigning the study record a unique ID number, which is stored in the identifier field of the study record.

At step 242, the citation information, such as the author and publication date for the study is extracted, and placed in the citation information field in the study record.

At step 243, an abstract is prepared for the study, and is placed in the patient readable abstract field of the study record. The abstract may be copied directly from the paper in which the study appeared, if the paper's abstract is suitable for use by a patient. Alternatively, if the paper's abstract is deemed too complex for patient use, a new abstract for the study may be prepared.

At step 244, input parameters for the study are extracted, and pointers to the extracted input parameters are placed in the input parameters field of the study record. If an extracted input parameter is identical to an existing input parameter that has already been extracted from another study, a pointer to the existing input parameter record may be used. Otherwise, a new input parameter record, as described hereinabove with reference to FIG. 5 must be created, and the fields of the new input parameter record must be populated with information on the input parameter. Populating the fields of an input parameter record may require a skilled technician or scientist to decide on appropriate selections for the input parameter, to decide in which input forms the input parameter should be included, and to write the display code, validation code, and reconstruction code for the input parameter, if necessary.

In step 245, the output parameters for the study are extracted, and pointers to the output parameters are placed in the output parameters field of the study record. Generally, differences between studies require that the output parameters from each study be separately extracted, even if the output parameters are nearly identical. Thus, it is typically necessary to create a new output parameter record, as described hereinabove with reference to FIG. 6, for each output parameter extracted from a study.

It is then necessary to populate the fields of the output parameter record with information extracted from the study, or selected by the technician or scientist who is extracting the output parameter. Some expertise may be required to assign the proper super-category to an output parameter. Additionally, it may be necessary to create new super-categories if there is no existing super category that is appropriate for the extracted output parameter.

At step 246, any output calculations or output tables associated with the study are extracted, and placed in the output calculations or output tables fields of the study record. The process of extracting calculations and tables from a study may require an expert to interpret the study, and prepare calculations or tables that map values of the study's input parameters to values of the study's output parameters. Depending on the study, it may be necessary to train a neural network and store the neural network in a table. The level of expertise and effort required to extract calculations and tables from a study generally will vary according to the study. At one end, the study may directly provide calculations or tables, which may simply be copied. At the other end, expert statistical or mathematical analysis may be required to extract the required calculations or tables.

In step 247, the study is assigned an output category, based on the nature of the study. The selected output category is placed in the output category field of the study record.

In step 248, the study is assigned a treatment category, according to the treatment applied to the study population. The selected treatment category is stored in the treatment category field of the study record.

In step 249, statistical information is collected from the paper for entry into the statistical field of the study record. The statistical information extracted may include p-values, mean values, standard deviations, population distributions, median values, sensitivity, and specificity. Information on the study populations such as the size of the study population, is also extracted in this step.

In step 250, a determination is made on the type of combination analysis to be used with the study. Certain combination analysis techniques, such as meta-analysis, may only be available if the proper statistical information is available from the paper. Meta-analysis, for example, may only be applied if the statistical information includes either p-values, means and standard deviations, or population distributions.

Finally, in step 251, a pointer to the completed study record in study table 37 of literature dataset 36 is sorted into other datasets, according to the study's output category. Database 22 may contain a dataset for each of the output categories to which a study may be assigned. Thus, for the exemplary prostate cancer system, database 22 would contain a staging dataset, an outcome dataset, a quality of life dataset, a complications dataset, and an alternatives dataset, in addition to the literature dataset. A reference to the study record is placed in a table in the appropriate dataset that associates each output category with all of the study records that address that output category. Thus, in the prostate cancer system, the staging dataset would contain a table containing references to all studies in literature dataset 36 having staging as their output category.

The Treatments Dataset

In addition to containing data extracted directly from medical literature, database 22 contains a dataset containing information on various treatments, and the rules (indications) that determine whether a particular treatment is appropriate. This treatments dataset is used by the system during profile generation to determine which treatments are suitable for use by a particular patient. The rules that determine whether a particular treatment is appropriate are obtained from experts in the treatment of the disease being handled by the system. Alternatively, the rules in the treatment dataset may be altered for each individual patient, based on the patient's preferences, the rules employed by the patient's personal physician, or the rules employed by the patient's insurance carrier.

Figure 9:
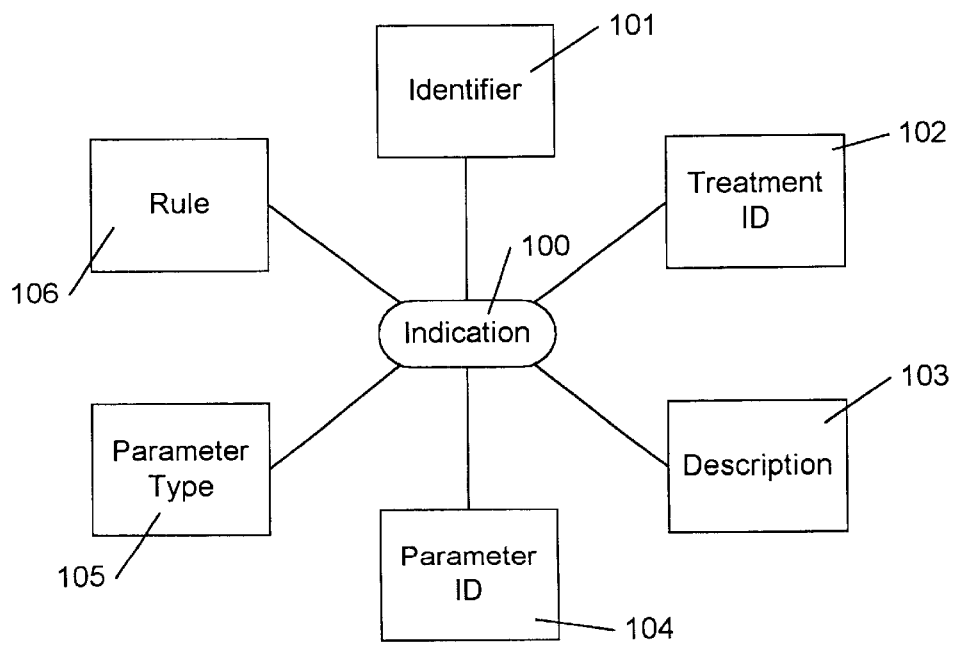
FIG. 9 shows the structure of a record in the treatment indications table in the medical database.

The treatments dataset contains an indications table that contains the indications for each of the treatments. FIG. 9 shows the fields in the indications table of the treatments dataset in database 22. Indications record 100 has fields for an identifier, a treatment ID, an indicator description, an indicator rule, a parameter ID, and a parameter type.

Identifier field 101 contains a unique identifier for each record in the indications table. Fields in other tables that reference records in the indications table may use the values stored in identifier field 101 to point to a particular record in the indications table.

Treatment ID field 102 contains the identifier of the treatment indicated by the conditions stored in the indications record. For example, if the indication relates to radical prostatectomy, treatment ID field 102 would contain an identifier for the radical prostatectomy treatment.

Description field 103 contains a textual description of the indication. For example, if an indication for radical prostatectomy is that the patient should have a life expectancy greater than ten years, description field 103 may contain the text "Life expectancy should be greater than 10 years."

Parameter ID field 104 identifies the parameter that must be tested for the indication. Thus, if using the life expectancy indication for radical prostatectomy described above, parameter ID field 94 would contain an identifier for the "life expectancy" parameter. Parameter type field 105 identifies the type of the parameter, which may be either an input parameter, or a super-category value. If parameter type field 105 indicates that the parameter is an input parameter, then parameter ID field 104 will point to one of the input parameters. Otherwise, if parameter type field 105 indicates that the parameter is a super-category, then parameter ID field 104 will point to one of the super-categories. In the "life expectancy" example, parameter type field 95 would indicate that the parameter is a super-category, since "life expectancy" is a super-category in the exemplary prostate cancer system.

Rule field 106 contains the condition on the input parameter that must be satisfied for the indication to be positive. The condition is written in a computer-readable format. For the "life expectancy" example, the rule would be ">=10". Thus, if the life expectancy super-category has a value greater than or equal to ten, the condition will be satisfied, and this indication for radical prostatectomy will be positive.

Table 4 shows a portion of the indications table from the prostate cancer system showing the indications for radical prostatectomy. As described in detail hereinbelow, during the process of preparing an individualized profile, the conditions listed in the indications table will be tested. If all of the indications shown in Table 4 are positive, then radical prostatectomy will be listed in the report as a viable treatment option.

Many of the fields of the indications table may be implemented using pointers to records in tables that associate information with ID numbers, rather than using the information itself. For example, in a preferred embodiment, parameter ID field 104 may contain the ID number of the parameter being used in either input parameters table 38, or a table containing information on the super-categories (not shown). Thus, the entry in Table 4 that uses the "General Health" input parameter contains the number "35," which is the unique identifier for the "general health" input parameter, as shown hereinabove in Table 2. A similar technique could be used for any of the fields in the table, except the identifier field.

Stage II: Profile Generation

Once database 22 has been populated with sufficient data from studies, and the available treatments have been entered into the treatments dataset, the system may be made available to patients, for generating individualized profiles. Collection of information from patients and generation of profiles are interactive processes, and are preferably performed over the Internet, or through some other communications medium.

Collection of Information from the Patient

Figures 10, 11:
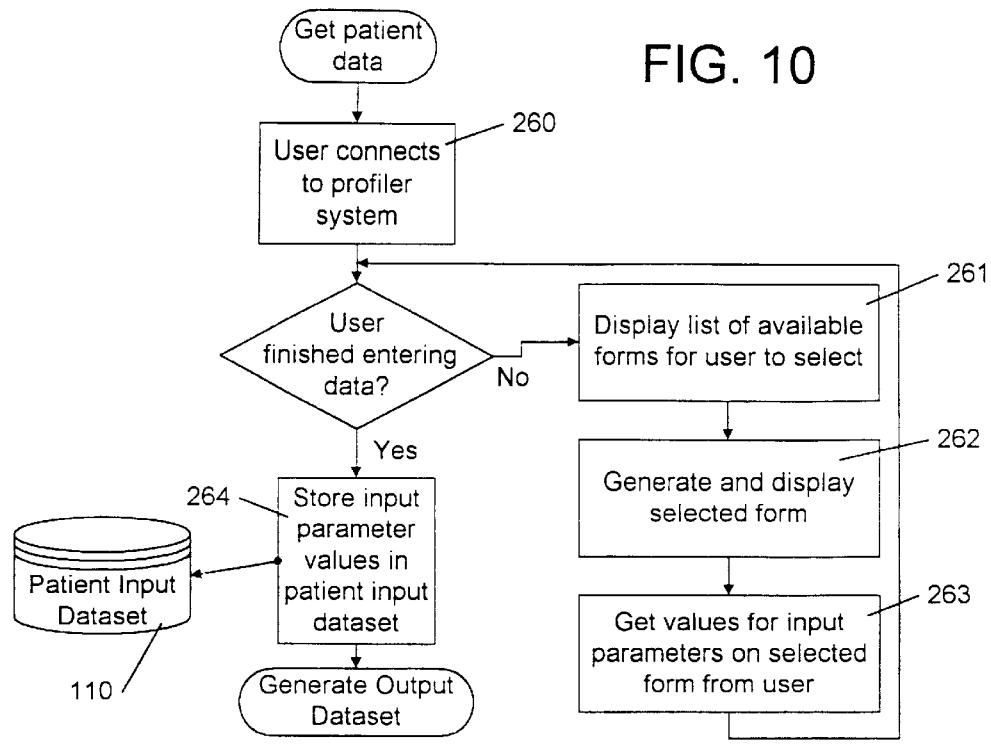
FIG. 10 is a flowchart of the process for generating input forms and obtaining values for input parameters from a patient.
FIG. 11 is an illustrative example of a portion of an input form.

The first step in generating a profile is collecting information from the patient to build a patient input dataset. Referring to FIG. 10, a preferred process of gathering information from the patient is described, in which a user interacts with the system of the present invention over the Internet to gather information.

In step 260, the user connects to the profiler system, and provides the system with basic information, such as his or her name, account ID (if an account has already been established), and payment information, such as a credit card number. When this information is entered, at step 261, the user is given a choice of forms to complete, to provide the system with the information that is needed to generate a profile. For the exemplary prostate cancer system, such forms may include a form for entering the results of blood tests, a form for entering the results of a doctor's exam, a form for entering the results of imaging workups, a form for entering demographic information, a form for entering information on quality of life issues, and a form for entering information on comorbid issues.

When the user selects a form, the system generates and displays the selected form at step 262 by using a table in database 22 that has been constructed for each form. This table (not shown) contains the identifiers of each of the input parameters to be included in the form, and the order in which the input parameters are to be displayed in the form. For each of the input parameters, the system displays the name of the parameter (retrieved from name field 57 of the input parameter), and an input box for the parameter, which may contain the current value (if any) of the input parameter. The input box is displayed in the form by executing the display code for the parameter, retrieved from display code field 61. If a value for the parameter is displayed, it may be necessary to first execute the parameter's reconstruction code, retrieved from reconstruction code filed 63. This process is repeated for each parameter in the selected form.

At step 263, the user enters values for the input parameters. For each input parameter value entered, the validation code for the parameter retrieved from validation code field 62 is executed. If the validation code indicates that the value entered is not valid, the value is rejected, and the user is asked to enter another value for that input parameter. Steps 261–263 are repeated until the user is finished entering data. At step 264, the data are stored in patient input dataset 110.

FIG. 11 shows some example parameter inputs from a "Pathology" input form for the exemplary prostate cancer system. The parameter names in column 117 of form 115 are retrieved from name field 57 of the input parameter records associated with the form. Each of the parameter names in column 117 forms a clickable link to a glossary definition explaining the parameter. When a user clicks on the parameter name, the glossary text for the parameter (retrieved from glossary term field 58) is displayed. If the user leaves the mouse pointer over one of the names in column 117, a short description of the parameter (retrieved from description field 58) is displayed.

Some of the input fields in form 117, such as fields 119*a*, 119*b*, and 119*c* comprise pull-down lists of possible selections for an input parameter. These selections are retrieved from selections field 64 of the input parameter record.

Generation of the Output Dataset

Figure 12:
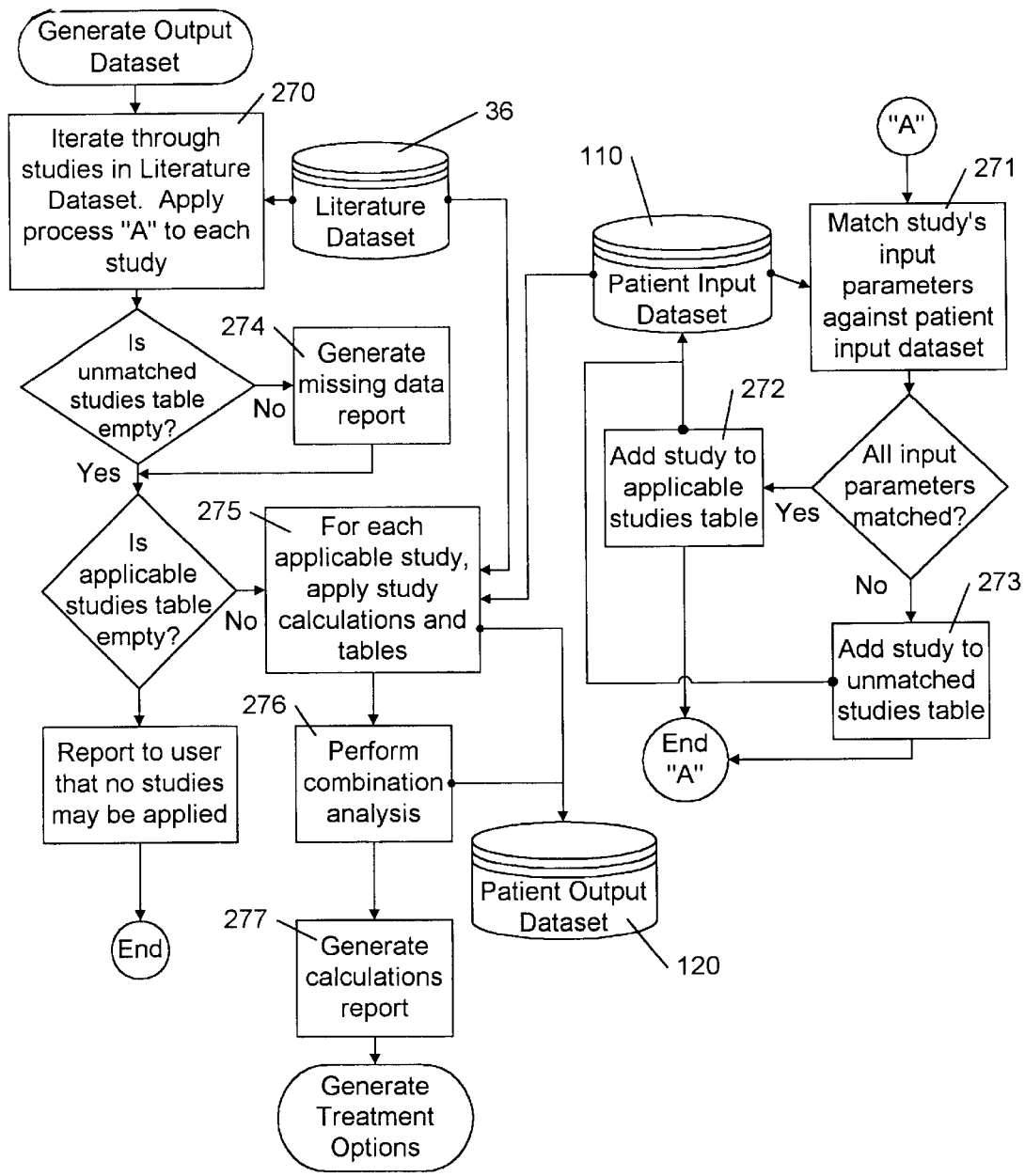
FIG. 12 is a flowchart of the process for generating output parameter values and "super-category" values from the input parameter values.

Referring to FIG. 12, a preferred method of generating an output dataset from patient input dataset 110 is described. At step 270, the system iterates through each of the studies in literature dataset 36, to determine which studies may be applied to the input dataset. This is done by matching the information in patient input dataset 110 against the input parameters for each study (step 271). If values for all of the input parameters of a study are present in patient input dataset 110, the ID of the study is added to an "applicable studies" table (not show) in patient input dataset 110 (step 272). Otherwise, if any of the input parameters for a study are not present in patient input dataset 110, the study is considered "unmatched", and the system preferably records the study's ID, the number of missing input parameters, a list of the missing input parameters, the output category of the study, and the size of the study population. This information is recorded in an "unmatched studies" table in patient input dataset 110 (step 273), and is used to generate missing data reports.

If the unmatched studies table is not empty, then, at step 274, a missing data report is generated. The missing data report preferably includes the names of the missing input parameters, and the number of studies for which each of the missing input parameters is needed and the total study population for those studies. Additionally, for each of the studies that could not be used due to a missing input parameter, the missing data report preferably lists the output categories of the study, the title of the study, the study population, and the required input parameters for the study. This information is sent to the patient, who may enter values for any missing input parameters, or may consult with his or her physician to obtain values for the missing input parameters.

If the applicable studies table is not empty, then at step 275, the system iterates through each study in the applicable studies table. For each of the studies, the system applies any calculations from the study (retrieved from output calculations field 47) and any tables from the study (retrieved from output tables field 46) to the values of the input parameters stored in patient input dataset 110 to generate values for the study's output parameters. Depending on the output calculations and output tables, this step may require complex computations to be performed, and may include application of advanced techniques such as neural networks to the values of the input parameters. Each output parameter value is stored in patient output dataset 120 in an output values table (not shown) that contains the value of the output parameter, a pointer to the study that generated the output parameter, and a pointer to the output parameter record in output parameters table 39 that contains information (such as name, and super category) on the output parameter.

At step 276, the system applies combination analysis to the output parameter values stored in patient output dataset 120 to generate combined values for the super-categories associated with each of the output parameters. This combination analysis may be performed using any of a variety of methods, depending on the combination rule associated with the study that generated each output parameter value (retrieved from combination rule field 51 of study records). The combination rule may indicate use of a simple method, such as averaging; a complex statistical method, such as meta-analysis; or an advanced technique such as fuzzy logic or fuzzy sets. Alternatively, the combination rule may indicate that combination is to be handled interactively, by reporting the values of the output parameters associated with each super category to the patient, and permitting him or her to specify what the combined super-category value should be. Combined super-category values are stored in patient output dataset 120.

Finally, in step 277, the system generates a calculations report, which may be displayed to the patient. The calculations report preferably contains information on the number of studies applied, the input parameter values for each study, the output parameter values for each study, and the super-category values computed by combination analysis.

Generating the Treatment Options

Figure 13:
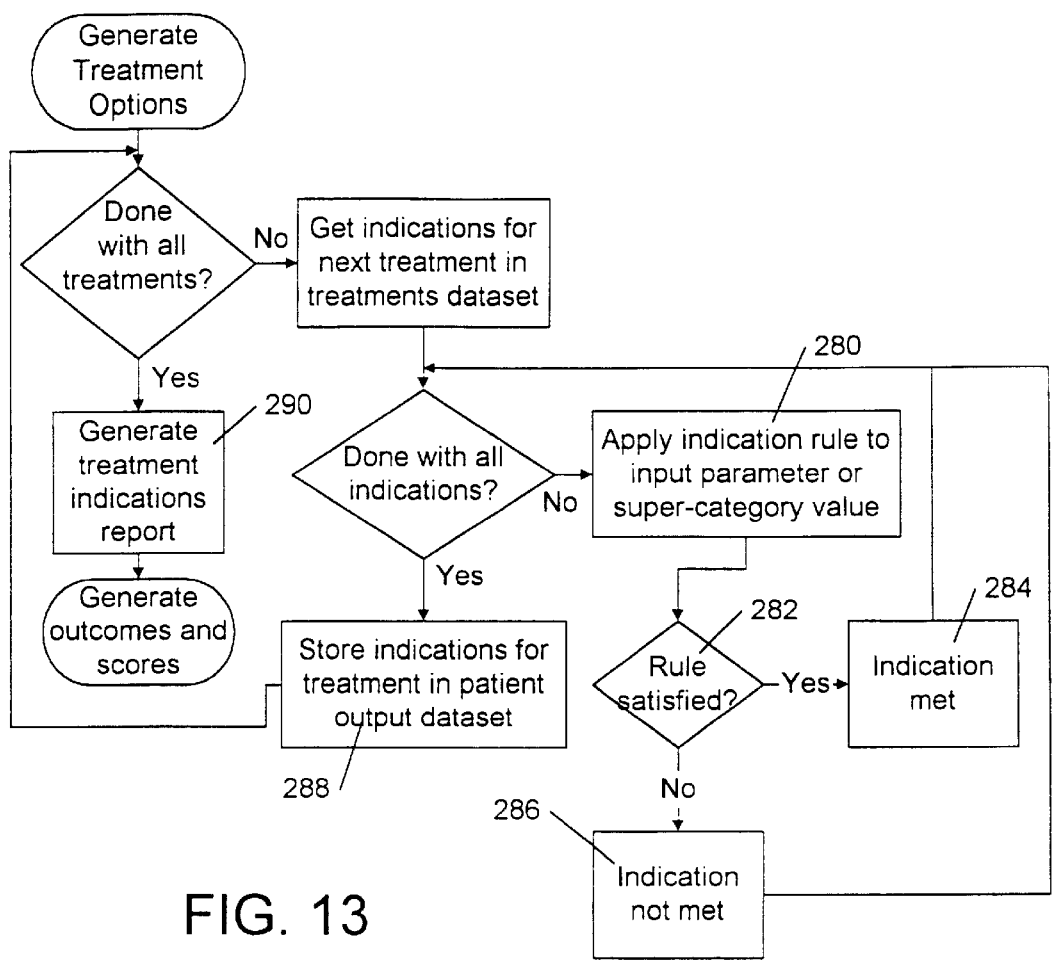
FIG. 13 is a flowchart of the method for generating treatment options.

Once the patient output dataset has been generated, the system generates treatment options, based on the super-category values, input parameter values, and treatment indications in the treatments dataset. FIG. 13 depicts a method that may be used for generating the treatment options.

The system steps though each of the treatments in the treatments dataset, and for each of the treatments, through each of the indications for that treatment. At step 280, the system applies the rule for the indication currently being examined against the value of a super category or the value of an input parameter (as specified in parameter type field 105—see FIG. 5), to see whether the indication is met.

In step 282, the system checks to see if the input parameter or super category value meets the indication rule. If so, the system marks the indication as being met (step 284). Otherwise, the system marks the indication as not being met (step 286).

When all the indications for a treatment have been determined, at step 288, the system stores the information in a treatment indications table (not shown) in patient output dataset 120. Treatments for which all of the indications were met are probably the best treatment options available to this patient. Treatments for which most of the indications were met also may be applied. Treatments for which most of the indications are not met are not deemed to be good treatment options for this patient.

At step 290, when all the available treatments have been checked, the system generates a treatment indications report, which may be displayed to the patient. For each available treatment, the treatment indications report preferably includes a description of each indication (retrieved from description field 103 of the indication records), the rule for each indication (from rule field 106), the value of the input parameter or super category referenced by each indication, and whether the indication was met or not. Treatments in the treatment indication report are preferably sorted according to how many of the treatment indications were met, with treatments for which all or most of the indications were met appearing first.

Generating Treatment Outcomes and Scores

Figure 14:
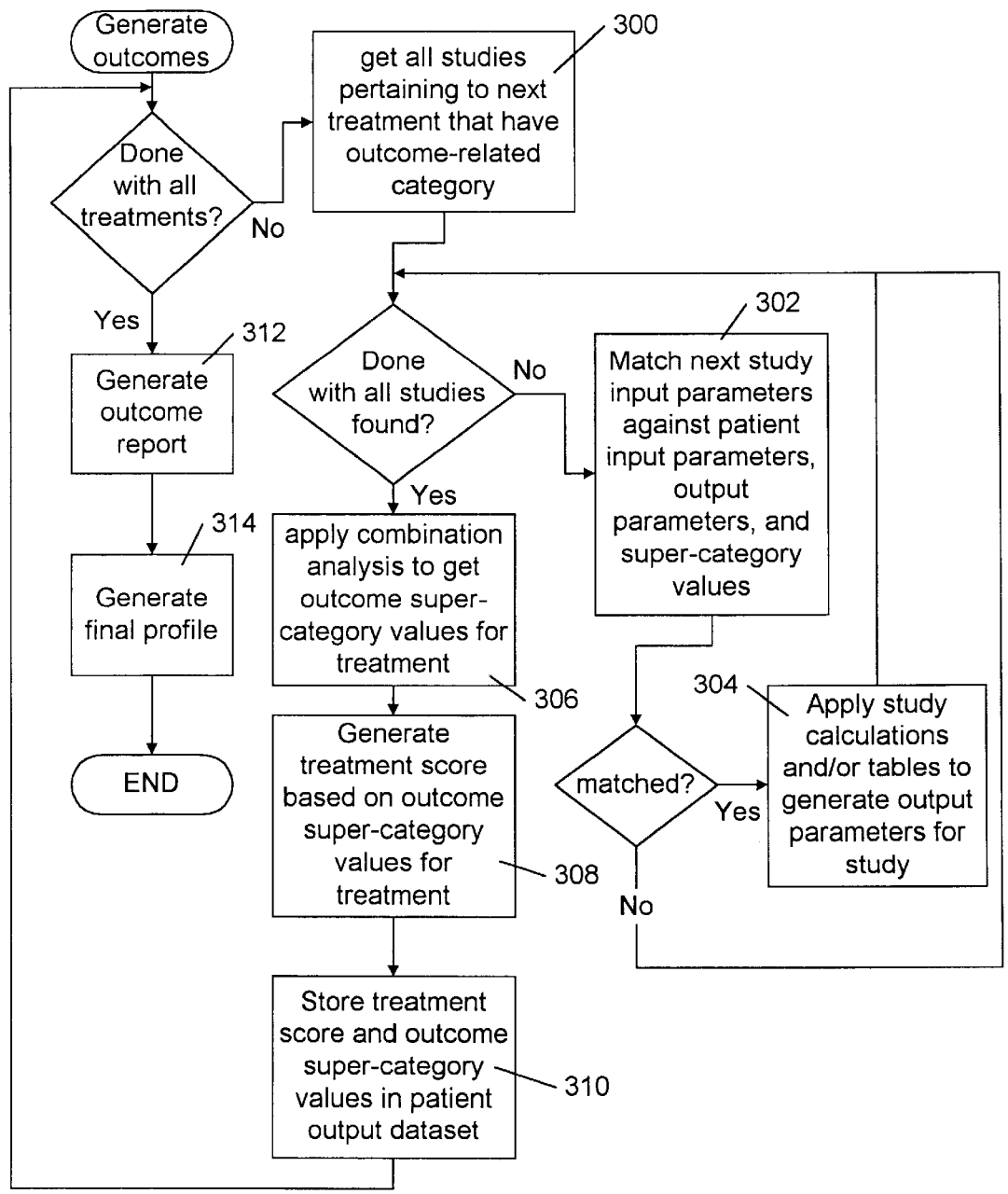
FIG. 14 is a flowchart of the method for generating information on the probable outcome of treatments, and for generating the profile.

Once the treatment options have been generated, the system applies the data in literature dataset 36 to the treatments to generate information on the likely outcome for each treatment. The process used to generate the outcome is similar to the process used to generate values for the output parameters, and is described with respect to FIG. 14.

At step 300, for each treatment, the system iterates through the studies in literature dataset 36 that apply to that treatment (as indicated in treatment category field 49), and that have an output category related to outcome. For each study that meets these criteria, the system matches the study's input parameters against available values of input parameters supplied by the user, as well as values of output parameters and super categories (step 302).

At step 304, if all the input parameters are matched, the system applies any calculations or tables from the study to the values of the input parameters to generate values for the study's output parameters. Depending on the output calculations and output tables, this step may require complex computations to be performed, and may include application of advanced techniques such as neural networks to the values of the input parameters. The output parameter values are stored in patient output dataset 120 in a treatment outcome table (not shown).

When all of the studies for a treatment have been used to compute output parameter values, at step 306, the system applies combination analysis to determine values for each of the super categories related to outcome. For the exemplary prostate cancer system, outcome super categories preferably include life expectancy, PSA Recurrence, Disease Free Survival (at six month intervals to five years), quality of life, and complications.

At step 308, the outcome super category values are used to determine an overall treatment score for each treatment. This may be accomplished through any of a variety of methods, including taking a weighted average of the outcome values, applying rules to determine the score from the values, applying fuzzy sets to determine the overall score from the values, or by any other calculation method that derives a single score from numerous scores. Alternatively, an interactive method may be employed, such as displaying the super category values to the user, and asking him or her to rank the treatments based on the super category scores.

At step 310, the information on the outcome super category values and overall treatment scores, as well as information on the studies applied for each treatment to generate the scores is stored in patient output dataset 120.

At step 312, an outcome report is generated, and may be displayed to the patient. For each treatment, the outcome report preferably contains the treatment score, the values for the outcome super categories for the treatment, and information on individual experiences of other patients who have undergone the treatment.

Finally, at step 314, the individualized profile is generated, and displayed or sent to the patient. In a preferred embodiment, the individualized profile preferably comprises an interactive web page that permits the patient to view the data in the profile, and to click on links to view more detailed information. The individualized profile contains all of the reports described above, including the missing data report, the calculations report, the treatment indications report, and the outcome report. Additionally, the individualized profile contains patient-readable information on each of the studies applied (preferably available through links from a summary of the studies), and an "executive summary", in which the super-category values for each category, and the applicability and outcome for each treatment are listed in a compact form.

All of the information stored in the patient input dataset and the patient output dataset is stored on the system for a period of time. During this period, which may be as long as several years, the patient may change or update the information, and may generate updated reports or profiles.

The personalized profile is intended to be used by a patient to augment information available from his or her physician, and is not meant to be used without a physician's advice. Once the profile is generated, the patient should discuss the profile with his or her physician. Based on this discussion, additional information may become available to the patient, who may provide this additional information to the system to generate updated profiles.

Figure 15:
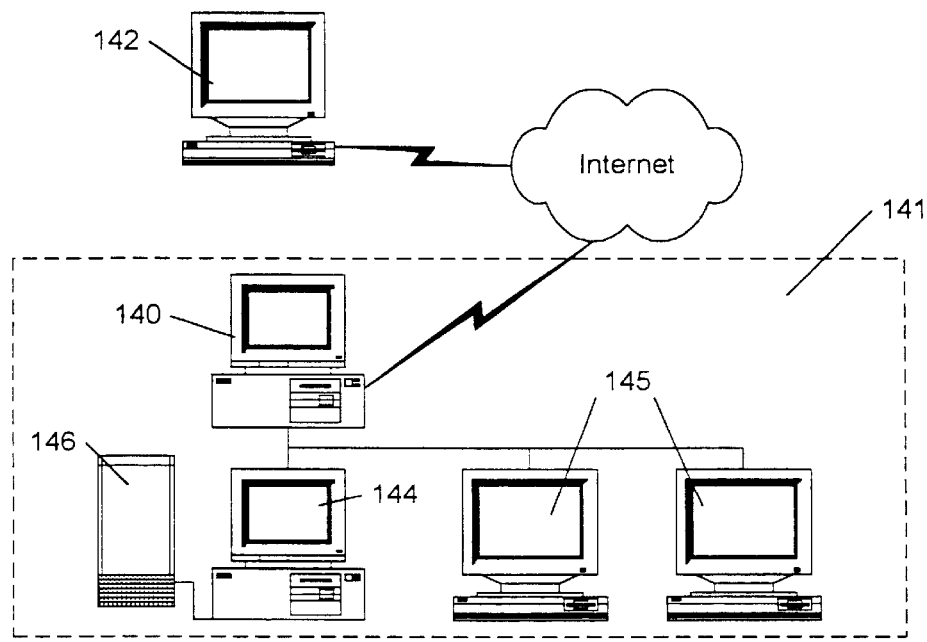
FIG. 15 shows an illustrative computer network on which the database and methods of the present invention may be implemented.

FIG. 15 depicts an illustrative computer system and network on which the system of the present invention may be implemented. Internet server 140 comprises a computer connected to the Internet via a high-speed connection, and is also connected to LAN 141. Internet server 140 preferably runs a standard HTTP server application, such as Apache, which is available for free from the Apache organization at "http://www.apache.org". Internet server 140 accepts HTTP connections from computers on the Internet, and sends web pages across the Internet to client computers, such as client computer 142.

Internet server 140 also runs a variety of scripts (such as Java "servlets" or CGI scripts) to interact with users across the Internet, to dynamically build web pages, and to access data stored on database server 144. Most of the routines for interacting with a patient, and for generating an individualized profile based on information provided by the patient, are stored and executed on Internet server 140.

Database server 144 comprises a computer system connected to LAN 141 that provides access to database 22, which is stored on RAID array 146. Database server 144 executes database software that permits other computers to access database 22 over LAN 141.

LAN 141 may also be connected to additional computers 145, that may be used, for example, to enter data extracted from studies into database 22. Most of the functions that may be performed using computers 145 connected to LAN 141 may also be performed over the Internet.

Patients use a personal computer connected to the Internet, such as client computer 142, to access the system of the present invention. Client computer 142 executes standard Internet browser software, such as Netscape Navigator, by Netscape Communications Corporation, of Mountain View, Calif. Client computer 142 uses the browser software to interact with Internet server 140 across the Internet, and to display web pages provided by Internet server 140 to the patient. The input forms generated by the system of the present invention, as well as the reports and profile generated by the system are displayed to the patient by the browser software running on client computer 142.

It should be understood that the network configuration discussed with reference to FIG. 15 is for purposes of illustration only. It would be possible, for example, to combine database server 144 with Internet server 140. Additionally, database 22 could be stored on a normal hard drive or other magnetic media, an optical disk, or in a distributed fashion on computers 145 on LAN 141, rather than on RAID array 146. The exact configuration of LAN 141, or the specific software and protocols used on the computers connected to LAN 141 all may be changed without departing from the present invention.

It will be apparent to one skilled in the art that the above-described methods and apparatus have uses beyond providing patients with information. For example, doctors and clinicians may benefit from using the system of the present invention to assist them in advising patients. The information on medical research literature provided by the system may be especially helpful to medical professionals or students.

Although preferred illustrative embodiments of the present invention are described above, it will be evident to one skilled in the art that various changes and modifications may be made without departing from the invention. For instance, although many of the examples refer to a system for generating profiles for prostate cancer patients, it will be understood that the above-described system may be applied to nearly any disease, depending on the availability of studies to build the medical database. Additionally, minor variations of the structure of the database, or of the algorithms used to generate the profiles may be made without significantly affecting the overall structure or operation of the system. It is intended in the appended claims to cover all such changes and modifications that fall within the true spirit and scope of the invention.

What is claimed is:

1. A method of generating individualized medical profiles for patients, the method comprising:

selecting medical literature for inclusion in a medical database, based on a set of predetermined inclusion criteria;

extracting data from studies in the selected medical literature for addition to the medical database, the data extracted for each study including one or more input parameters, one or more output parameters, and one or more algorithms;

compiling a set of input parameters comprising one or more input parameters extracted from each study, a set of output parameters comprising one or more output parameters extracted from each study, and a set of algorithms comprising one or more algorithms extracted from each study;

collecting information from a patient to provide values for a subset of the set of input parameters;

matching the subset of input parameters to the one or more input parameters for each study in the medical database to produce a set of applicable studies;

using a first subset of the set of algorithms corresponding to the applicable studies on the values of the subset of input parameters to produce values for a subset of the set of output parameters corresponding to the applicable studies; and generating an individualized medical profile based on the values of the subset of output parameters.

2. The method of claim 1, further comprising:

adding data on treatments and treatment indications to the medical database;

using the values of the subset of output parameters to determine which treatment indications are met; and generating a treatment indications report wherein the treatment indications for each treatment are listed, along with a mark showing whether each treatment indication was met, wherein generating the individualized medical profile further comprises including the treatment indications report in the individualized medical profile.

3. The method of claim 2, further comprising:

applying combination analysis to the values of the subset of output parameters to produce a set of combined super-category values, wherein using the values of the subset of output parameters to determine which treatment indications are met comprises using the set of combined super-category values to determine which treatment indications are met.

4. The method of claim 3, wherein using the values of the subset of output parameters to determine which treatment indications are met further comprises using the values of the subset of input parameters to determine which treatment indications are met.

5. The method of claim 2, wherein adding data on treatments and treatment indications to the medical database comprises adding a rule to the medical database for each indication, the rule determining whether the treatment indication is met.

6. The method of claim 5, wherein using the values of the subset of output parameters to determine which treatment indications are met further comprises using the rule for each treatment indication to determine whether the treatment indication is met.

7. The method of claim 2, further comprising generating outcome information for each treatment, and including the outcome information in the individualized medical profile.

8. The method of claim 7, wherein generating outcome information for each treatment comprises generating an outcome score for each treatment.

9. The method of claim 7, wherein generating outcome information for each treatment comprises:

determining which studies in the medical database are applicable to the outcome of a treatment; and using a second subset of the set of algorithms corresponding to the studies that are applicable to the outcome of the treatment to produce output values indicative of the outcome of the treatment.

10. The method of claim 7, wherein the outcome information is stored in an individualized patient output dataset in the medical database.

11. The method of claim 2, wherein information on which treatment indications were met is stored in an individualized patient output dataset in the medical database.

12. The method of claim 1, wherein values of the subset of output parameters are stored in an individualized patient output dataset in the medical database.

13. The method of claim 1, wherein the first subset of algorithms comprise calculations or tables that map values of the subset of input parameters to values of the subset of output parameters.

14. The method of claim 13, wherein the tables optionally represent neural networks.

15. The method of claim 1, wherein matching the subset of input parameters to the one or more input parameters for each study further comprises:

compiling a list of unmatched studies, including each study for which the subset of input parameters does not match the one or more input parameters of the respective study; and using the list of unmatched studies to generate a missing data report.

16. The method of claim 1, wherein the method further comprises applying combination analysis to the values of the subset of output parameters to produce a set of combined super-category values.

17. The method of claim 16, wherein the combination analysis comprises a technique chosen from a set consisting of meta-analysis, averaging, fuzzy logic, fuzzy sets, and interactive combination techniques.

18. The method of claim 17, wherein the data extracted for each study includes statistical information, and the statistical information is used to determine which combination analysis technique is applied.

19. The method of claim 1, wherein collecting information from the patient comprises:

generating an input form having input fields for a plurality of input parameters from the set of input parameters; and extracting values for the plurality of input parameters from values entered by the patient into the input fields.

20. The method of claim 19, wherein each one of the set of input parameters in the medical database includes display code for displaying that input parameter, and generating the input form comprises executing the display code for each one of the plurality of input parameters in the form.

21. The method of claim 19, wherein each one of the set of input parameters in the medical database includes validation code for validating that input parameter, and extracting values for the subset of input parameters from data entered by the patient comprises executing the validation code for each value entered by the patient.

22. The method of claim 19, wherein each one of the set of input parameters includes an identifier for a form on which that input parameter should appear.

23. The method of claim 1, wherein selecting medical literature for inclusion in the medical database further comprises:

providing the medical literature to a review board including a plurality of reviewers;

having each reviewer assign each study in the medical literature a score, based on the predetermined inclusion criteria; and determining which studies should be included in the medical database based on the scores assigned by the reviewers.

24. The method of claim 23, wherein determining which studies should be included comprises computing an average score for each of the studies, and including studies for which the average score exceeds a predetermined threshold.

25. The method of claim 1, wherein the predetermined inclusion criteria comprise one or more of: criteria based on the objectives of the study, on the study population, on the description of the methods used in the study, on the results of the study, on the statistical significance of the study, and on the ability to summarize the results of the study in the form of a calculation or table.

26. The method of claim 1, wherein the data extracted for each study further includes citation information, a patient readable abstract, statistical information, and information on the study population.

27. A computer system for generating individualized medical profiles for patients, the computer system comprising a server storing a series of programmed routines, the computer system further comprising:

a medical database containing information on studies extracted from medical literature, the information comprising a set of input parameters, a set of output parameters and a set of algorithms, each study having one or more input parameters, one or more output parameters, and one or more algorithms;

a data collection routine that collects information from a patient to provide values for a subset of the set of input parameters;

a matching routine that matches the subset of input parameters for which values are collected from the patient with the set of input parameters to produce a set of applicable studies;

a computation routine that uses algorithms from the applicable studies on the values of the subset of input parameters to produce values for a subset of the set of output parameters; and an output routine that generates an individualized medical profile based on the values of the subset of output parameters.

28. The computer system of claim 27, wherein the medical database further comprises data on treatments and treatment indications from the medical database, the computer system further comprising:

a treatment routine that uses the values of the output parameters to determine which treatment indications are met and generates a treatment indications report wherein the treatment indications for each treatment are listed, along with a mark showing whether each treatment indication was met.

29. The computer system of claim 28, wherein the treatment routine applies combination analysis to the values of the subset of output parameters to produce a set of combined super-category values and uses the set of combined super-category values to determine which treatment indications are met.

30. The computer system of claim 28, wherein the treatment routine uses the values of the subset of input parameters to determine which treatment indications are met.

31. The computer system of claim 28, wherein the medical database stores a rule for each treatment indication and the treatment routine uses the rule to determine whether the treatment indication is met.

32. The computer system of claim 28, wherein the computer system further comprises an outcome routine that generates outcome information for each treatment, and the output routine includes the outcome information in the individualized medical profile.

33. The computer system of claim 32, wherein the outcome routine determines which studies in the medical database are applicable to the outcome of a treatment and uses the algorithms from the studies that are applicable to the outcome of the treatment to produce output values indicative of the outcome of the treatment.

34. The computer system of claim 33, wherein the algorithms comprise calculations or tables that map values of input parameters to values of output parameters.

35. The computer system of claim 34, wherein the tables optionally represent neural networks.

36. The computer system of claim 27, wherein the computer system further comprises:

a routine that compiles a list of unmatched studies, including all studies for which the information collected from the patient does not match the one or more input parameters of each one of the studies and uses the list of unmatched studies to generate a missing data report.

37. The computer system of claim 27, wherein the computation routine further comprises a combination routine that applies combination analysis to the values of the subset of output parameters to produce a set of combined super-category values.

38. The computer system of claim 37, wherein the combination routine performs combination analysis using a technique chosen from a set consisting of meta-analysis, averaging, fuzzy logic, fuzzy sets, and interactive combination techniques.

39. The computer system of claim 37, wherein the combination routine accesses statistical information on the studies from the medical database and uses the statistical information to determine which combination analysis technique to apply.

40. The computer system of claim 27, wherein the data collection routine generates an input form having input fields for a plurality of input parameters and extracts values for the plurality of input parameters from values entered by the patient into the input fields.

41. The computer system of claim 40, wherein each one of the set of input parameters in the medical database includes display code for displaying that input parameter, and the data collection routine generates the input form by executing the display code for each one of the plurality of input parameters in the form.

42. The computer system of claim 40, wherein each one of the set of input parameters in the medical database includes validation code for validating that input parameter, and the data collection routine extracts values for the plurality of input parameters from data entered by the patient by executing the validation code for each value entered by the patient.

43. The computer system of claim 40, wherein each one of the set of input parameters includes an identifier for a form on which that input parameter should appear.

* * * * *